United States Patent [19]

Taylor et al.

[11] Patent Number: 4,920,125

[45] Date of Patent: Apr. 24, 1990

[54] L-GLUTAMIC ACID DERIVATIVES

[75] Inventors: Edward C. Taylor, Princeton, N.J.; Philip M. Harrington, Plainwell, Mich.; Chuan Shih, Indianapolis, Ind.

[73] Assignee: The Trustees of Princeton University, Princeton, N.J.

[21] Appl. No.: 399,993

[22] Filed: Aug. 29, 1989

[51] Int. Cl.$^5$ .................. C07D 239/48; C07D 239/49; A61K 31/505
[52] U.S. Cl. ..................................... 514/272; 544/320
[58] Field of Search .......................... 514/272; 544/320

[56] References Cited

U.S. PATENT DOCUMENTS 4,339,453  7/1982  Grier et al. .......................... 514/272

Primary Examiner—John M. Ford
Attorney, Agent, or Firm—Mathews, Woodbridge & Collins

[57] ABSTRACT

Pyrimidin-5-yl derivatives of L-glutamic acid are antineoplastic agents. A typical embodiment is N-(4-[5-(2,6-diamino-4-hydroxypyrimidin-5-yl)-butyl]-thien-2-ylcarboxy)-L-glutamic acid.

7 Claims, No Drawings

L-GLUTAMIC ACID DERIVATIVES

This invention pertains to derivatives of L-glutamic acid which are antineoplastic agents, to their preparation and use, and to intermediates useful in their preparation.

BACKGROUND OF THE INVENTION

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) and 5-deazaaminopterin has activity similar to that of amethopterin (Taylor et al., *J. Org. Chem.*, 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541). 10-Deazafolic acid, on the other hand, shows no significant activity (Struck et al., *J. Med. Chem.*, 1971, 14, 693) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 1979, 229) and 5,8,10-trideazafolic acid also shows only marginal activity against mouse L1210 leukemia (Oatis et al., *J. Med. Chem.*, 1977, 20, 1393). 5,10-Dideazaaminopterin and 5,10-dideaza-5,6,7,8-tetrahydroaminopterin, and the corresponding 5,10-dideazafolic acid derivatives are reported by Taylor et al., *J. Med. Chem.*, 28:7, 914 (1985).

DISCLOSURE OF INVENTION

The invention pertains to glutamic acid derivatives of the formula:

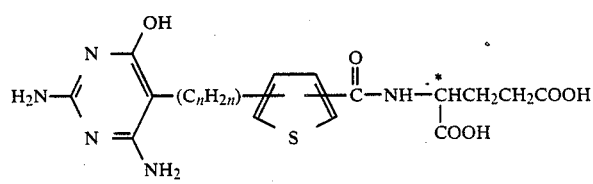

in which n has a value of 2 to 6; and the configuration about the carbon atom designated * is L; and the pharmaceutically acceptable salts thereof.

The invention also pertains to methods for the preparation of such compounds, to intermediates useful in those preparations, and to methods and compositions for the use of such compounds in combating neoplastic growth.

MODES FOR CARRYING OUT THE INVENTION

The compounds of Formula I exist in tautomeric equilibrium with the corresponding 4-oxo and compounds:

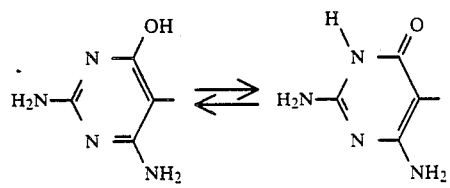

For convenience, the 3,4-dehydro-4-hydroxy form is depicted, and the corresponding nomenclature is used, throughout this specification, it being understood that in each case such includes the tautomeric 4(3H)-oxo forms.

The subscript n can have a value of from 2 to 6, thereby denoting a divalent alkylene group of 2 to 6 carbon atoms, such as ethylene, trimethylene, 1,2-propylene, 2,3-propylene, tetramethylene, 1,2-butylene, 2,3-butylene, pentamethylene, 1,2-pentylene, 2,3-pentylene, 1,3-pentylene, hexamethylene, 1,2-hexylene, 2,3-hexylene, 2,4-hexylene and the like. Preferably has a value of 3 to 5. The two monovalent carbon atoms preferably are separated by two carbon atoms; i.e., tetramethylene, 1,4-pentylene, 2,5 pentylene, and pentamethylene. It will be appreciated that a given branched alkylene group such as 1,4-pentylene can be oriented in either of two ways - with the branched carbon atom adjacent to the pyrimidin-5-yl group or adjacent to the depicted thienyl group.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like. Particularly preferred is the disodium salt.

The compounds can be prepared by hydrolysis of a 2,6-diamino-4-hydroxypyrimidin-5-yl-L-glutamic acid derivative of the formula:

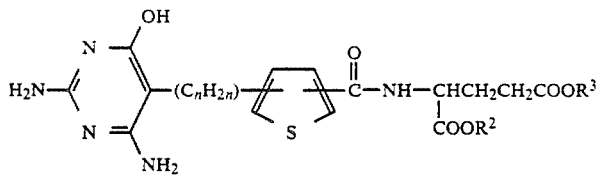
(II)

in which each of R² and R³ is a carboxylic acid protecting group, and n is as defined above.

Protecting groups encompassed by R² and R³ and reactions for their removal are described, for example, in "Protective Groups in Organic Chemistry", Plenum Press, London and New York (1973); Greene, "Protective Groups in Organic Synthesis", Wiley, New York (1981); "The Peptides", Vol. I, Schröder and Lubke, Academic Press, London and New York (1965); in "Methoden der organischen Chemie", Houben-Weyl, 4th Edition, Vol. 15/I, Georg Thieme Verlag, Stuttgart (1974). Carboxylic acid protecting groups can be, for example, esters conceptually derived from lower alkanols of from 1 to 6 carbon atoms, including those branched in the 1-position and those which are substituted with one or more aromatic groups such as phenyl, or with halo or alkoxy; e.g., methyl, ethyl, t-butyl, benzyl, 4-nitrobenzyl, diphenylmethyl, methoxymethyl, and the like esters. Silyl esters such as trimethylsilyl also can be employed.

The hydrolysis is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the product is initially formed as the dicationic glutamate salt and can be readily precipitated by adjustment of pH, as through acidification with, for example, acetic acid. The resulting products generally are crystalline or microcrystalline solids.

Compounds of Formula II can be prepared by coupling a compound of the formula:

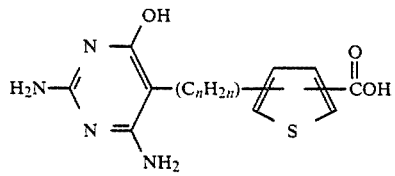
(III)

with a protected glutamic acid derivative of the formula:

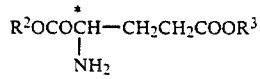
(IV)

utilizing conventional condensation techniques for the formation of peptide bonds, such as activation of the carboxylic acid group through formation of a mixed anhydride, treatment with DCC, or the use of diphenylchlorophosphonate.

Formation of the intermediate of Formula III can be accomplished by cyclization of an -cyano dicarboxylate of the formula:

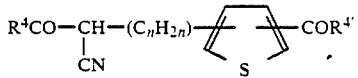
(V)

in which R⁴ and R⁴' are the same or different alkoxy group of 1 to 6 carbon atoms and n is as herein defined, with guanidine free base. Following formation of the pyrimidine ring, the R⁴' group can be removed through hydrolysis.

The intermediates of Formula V can be prepared by condensing an alkyl cyanoacetate of the formula:

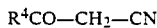
(VI)

with a mesityl ester of the formula:

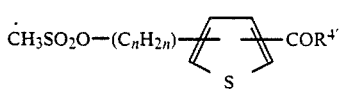
(VII)

in the presence of a strong base such as sodium hydride.

The mesityl ester intermediates of Formula VII can be obtained from hydroxy acid esters of the formula:

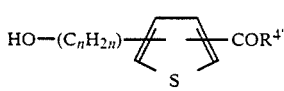
(VIII)

which are either known or can be prepared by known methods, as more fully exemplified below.

Typical compounds of the present invention include:
N-(4-[3-(2,6-diamino-4-hydroxypyrimidin-5-yl)propyl]-thien-2-ylcarboxy)-L-glutamic acid;
N-(4-[4-(2,6-diamino-4-hydroxypyrimidin-5-yl)butyl]-thien-2-ylcarboxy)-L-glutamic acid;
N-(5-[4-(2,6-diamino-4-hydroxypyrimidin-5-yl)butyl]-thien-2-ylcarboxy)-L-glutamic acid;
N-(5-[3-(2,6-diamino-4-hydroxypyrimidin-5-yl)propyl]-thien-2-ylcarboxy)-L-glutamic acid;
N-(5-[4-(2,6-diamino-4-hydroxypyrimidin-5-yl)butyl]-thien-3-ylcarboxy)-L-glutamic acid;
N-(4-[4-(2,6-diamino-4-hydroxypyrimidin-5-yl)butyl]-thien-3-ylcarboxy)-L-glutamic acid;
N-(4-[5-(2,6-diamino-4-hydroxypyrimidin-5-yl)pentyl]-thien-2-ylcarboxy)-L-glutamic acid;
N-(4-[3-(2,6-diamino-4-hydroxypyrimidin-5-yl)propyl]-thien-3-ylcarboxy)-L-glutamic acid;
N-(4-[5-(2,6-diamino-4-hydroxypyrimidin-5-yl)pentyl]-thien-2-ylcarboxy)-L-glutamic acid;

The compounds of Formula I contain a chiral center in the L-glutamic acid portion of the molecule. If no other chiral centers are present, the compounds are obtained in this configuration. The presence of one or more further chiral centers in —(C$_n$H$_{2n}$)— will lead to diastereomers. These diastereomers can be separated mechanically, as by chromatography, so that each is in a form substantially free of the other; i.e., having an optical purity of >95%. Alternatively, a mixture of diastereoisomeric compounds of Formula I is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidone-5-carboxylic acid, and the like.

The compounds of this invention have an effect on one or more enzymes which utilize folic acid, and in particular metabolic derivatives of folic acid, as a substrate. For example the $IC_{50}$ in whole cell human leukemia cell lines, CCFR-CEM, of N-(4-[4-(2,6-diamino-4-hydroxypyrimidin-5-yl)butyl]thien-2-yl)-L-glutamic acid is 0.076 µg/mL while that for N-(5-[4-(2,6-diamino-4-hydroxypyrimidin-5-yl)butyl]thien-2-yl)-L-glutamic acid is 0.002 µg/mL.

Cytotoxicity is reversed by addition of purines such as hypoxanthine or by addition of aminoimidazolecarboxamide but is not reversed by addition of thymidine, indicating specific inhibition in the de novo purine synthesis.

The compounds of Formula I can be used, alone or in combination, to treat neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides, psoriasis, and arthritis.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. In general, the compounds are administered in much the same fashion as methotrexite, but because of a different mode of action, can be administered in higher dosages than those usually employed with methotrexate. Dosage regimens must be titrated to the particular neoplasm, the condition of the patient, and the response but generally doses will be from about 10 to about 100 mg/day for 5-10 days or single daily administration of 250-500 mg, repeated periodically; e.g., every 14 days. Oral dosage forms include tablets and capsules containing from 1-10 mg of drug per unit dosage. Isotonic saline solutions containing 20-100 mg/ml can be used for parenteral administration.

The following examples will serve to further illustrate the invention.

EXAMPLE 1

N-(4-[4-(2,6-Diamino-4-hydroxypyrimidin-5-yl)butyl]-thien-2-ylcarboxy)-L-glutamaic acid.

A. Diethyl N-(4-[4-(2,6-Diamino-4-hydroxypyrimidin-5-yl)butyl]-thien-2-ylcarboxy)-L-glutanate.

A 25 mL round bottomed flask, equipped with a magnetic stirrer and gas inlet, was charged with 0.15 g (1.0 eq) of 4-[4-(2,6-diamino-4-hydroxypyrimidin-5-yl)butyl]thien-2-ylcarboxylic acid, 0.20 g (1.5 eq) of phenyl N-phenylphosphoramidochloridite, 0.25 g (5.0 eq) of N-methylmorpholine, and 15 mL of anhydrous N-methylpyrrolidone. The mixture was stirred at room temperature under a nitrogen atmosphere for 1 hour. To the resulting homogeneous solution was added 0.23 g (2.0 eq) of diethyl L-glutamate hydrochloride and stirring under nitrogen was continued for 24 hours. The solvent was removed by vacuum distillation and chloroform was added to the residue. The chloroform solution was washed with water. The organic extracts were combined, dried (magnesium sulfate), filtered, and concentrated under reduced pressure. Purification was carried out by flash chromatography eluting with 10% methanol/chloroform. Fractions homogeneous by TLC for the major component were combined and concentrated under reduced pressure to give 0.13 g (54.2%) of diethyl N-(4-[4-(2,6-diamino-4-hydroxypyrimidin-5-yl)butyl]thien-2-ylcarboxy)-L-glutamate as a pale yellow powder, m.p.: 94°–96° C.; IR (KBr, cm$^{-1}$): 3368, 3363, 3361, 3358, 3352, 3349, 3346, 3343, 1735, 1560, 1552, 1525, 1499, 1447, 1428, 1371, 1206, 1180; UV (Ethanol): $\lambda_{max}$=278 nm (epsilon=19,700), 248 nm (epsilon=13,300), 211 nm (epsilon=23,900), $^1$H NMR (CDCl$_3$, 300 MHz) delta 7.94 (s, 1H), 7.85 (d,J=7.8 Hz, 1H), 7.08 (s, 1H), 5.11 (bs, 2H), 4.67–4.73 (m, 1H) 4.55 (bs, 2H), 4.23 (q, J=7.2 Hz, 2H), 4.15 (q, J=7.2 Hz, 2H), 2.66–2.71 (m, 2H), 2.56–2.61 (m, 2H), 2.23–2.44 (m, 4H), 1.59–1.70 (m, 2H), 1.44–1.51 (m, 2H), 1.25–1.32 (m, 6H); MASS: M$^+$=494 (FD).

Other protected L-glutamic acid derivatives can be employed analogously. Thus from dimethyl L-glutamate and dipropyl L-glutamate there are obtained dimethyl N-(4-[4-(2,6-diamino-4-hydroxypyrimidin-5yl)butyl]thien-2-ylcarboxy)-L-glutamate and dipropyl N-4-[4-(2,6-diamino-4-hydroxypyrimidin-5-yl)butyl]thien-2-ylcarboxy)-L-glutamate.

B. N-(4-[4-(2,6-Diamino-4-hydroxypyrimidin-5-yl)butyl]-thien-2-ylcarboxy)-L-glutamic acid.

A 100 mL round bottomed flask equipped with a magnetic stirrer was charged with 0.11 g of diethyl N-4-[4-(2,6-diamino-4-hydroxypyrimidin-5-yl)butyl]thien-2-ylcarboxy)-L-glutamate in 40 mL of 1N sodium hydroxide. The reaction mixture was stirred at room temperature for 72 hours. The solution was acidified to pH 4 with hydrochloric acid and the resultant precipitate filtered, washed with water, and dried to give 0.07 g (70%) of N-(4-[4-(2,6-diamino-4-hydroxypyrimidin-5-yl)butyl]thien-2-ylcarboxy)-L-glutamic acid as a pale yellow powder, m.p.: 235°–236° C.; IR (KBr, cm$^{-1}$): 1711, 1661, 1620, 1557, 1546, 1520, 1503, 1412; UV (Ethanol): $\lambda_{max}$=277 nm (epsilon=7080), 247 nm (epsilon=4770), 211 nm (epsilon=8410); 1H NMR (d$_6$-DMSO, 300 MHz) delta 9.70 (bs, 1H), 8.52 (d, J=7.8 Hz, 1H), 7.74 (s, 1H), 7.34 (s, 1H), 5.87 (bs, 2H) 5.61 (bs, 2H), 4.28–4.34 (m, 1H), 2.55 (t, J=7.3 Hz, 2H), 2.03–2.07 (m, 1H), 1.88–1.94 (m, 1H), 1.51–1.58 (m, 2H), 1.28–1.34 (m, 2H); MASS: M+ =438 (FAB).

By following the procedures of Example 1, parts A and B, N-(4-[4-(2,6-diamino-4-hydroxypryimidin-5-yl)butyl]thien-3-ylcarboxy)-L-glutamic acid is obtained from 4-[4-(2,6-diamino-4-hydroxypyrimidin-5-yl)butyl]-thien-3-ylcarboxylic acid.

Similarly prepared from 4-[1-(2,6-diamino-4-hydroxypyrimidin-5-yl]pent-4-yl]thien-2-ylcarboxylic acid; 4-[3-(2,6-diamino-4-hydroxypyrimidin-5-yl)propyl]thien-2-ylcarboxylic acid; 4-[2-(2,6-diamino-4-hydroxypyrimidin-5-yl)ethyl]thien-2-ylcarboxylic acid; and 4-[6-(2,6-diamino-4-hydroxypyrimidin-5-yl)hexyl]thien-2-ylcarboxylic acid, there is obtained N-(4-[1-(2,6-diamino-4-hydroxypyrimidin-5-yl)pent-4-yl]thien-2-ylcarboxy)-L-glutamic acid; N-(4-[3-(2,6-diamino-4-hydroxypyrimidin-5-yl)propyl]thien-2-ylcarboxy)-L-glutamic acid; N-(4-[2-(2,6-diamino-4-hydroxypyrimidin-5-yl)-ethyl]thien-2-ylcarboxy)-L-glutamic acid; and N-(4-[6-(2,6-diamino-4-hydroxypyrimidin-5-yl)hexyl]-thien2-ylcarboxy)-L-glutamic acid;

EXAMPLE 2

N-(5-[4-2(2,6-Diamino-4-hydroxypyrimidin-5-yl)butyl]-thien-2-ylcarboxy)-L-glutamic acid.

By following the procedure of Example 1A, but allowing 5-[4-(2,6-diamino-4-hydroxypyrimidin-5-yl)butyl]thien-2-ylcarboxylic acid to react with diethyl L-glutamate, there is obtained diethyl N-(5-[4-(2,6-diamino-4-hydroxypyrimidin-5-yl)butyl]thien-2-ylcarboxy)-L-glutamate, m.p. 96°–98° C.; $^1$H NMR (CDCl, 300 MHz) delta 7.34 (d, J=3.4 Hz, 1H), 7.19 (d, J=7.5 Hz, 1H), 6.66 (d, J=3.4 Hz, 1H), 5.70 (bs, 2H), 4.80 (bs, 2H), 4.67–4.72 (m, 1H), 4.19 (q, J=7.1 Hz, 2H), 4.08 (q, J=7.1 Hz, 2H), 2.72–2.79 (m, 2H), 2.41–2.48 (m, 2H), 2.06–2.31 (m, 4H), 1.59–1.66 (m, 2H), 1.40–1.45 (m, 2H), 1.17–1.29 (m, 6H); MASS: M+ =494 (FD).

This ester is hydrolysed as described in Example 1B to yield N-(5-[4-(2,6-diamino-4-hydroxypyrimidin-5-yl)butyl]thien-2-ylcarboxy)-L-glutamate, m.p. 253°–256° C.; 1H NMR (d$_6$DMSO, 300 MHz) delta 9.68 (bs, 1H), 8.45 (d, J=7.1 Hz, 1H), 7.64 (d, J=3.6 Hz, 1H), 6.83 (d, J=3.6 Hz, 1H), 5.86 (bs, 2H), 5.60 (bs, 2H), 4.26–4.34 (m, 1H), 4.06–4.11 (m, 2H), 2.76 (t, J=7.3 Hz, 2H), 2.30 (t, J=7.7 Hz, 2H), 2.15 (t, J=6.8 Hz, 2H), 1.52–1.57 (m, 2H), 1.29–1.35 (m, 2H); MASS: M+ =438 (FAB).

Similarly obtained from 5-[4-(2,6-diamino-4-hydroxypyrimidin-5-yl)butyl]thien-3-ylcarboxylic acid is N-(5-[4-(2,6-diamino-4-hydroxypyrimidin-5-yl)butyl]thien-3-ylcarboxy)-L-glutamic acid.

Likewise by use of 5-[1-(2,6-diamino-4-hydroxypyrimidin-5-yl)pent-4-yl]thien-2-ylcarboxylic acid; 5-[3-(2,6-diamino-4-hydroxypyrimidin-5-yl)propyl]thien-2-ylcarboxylic acid; 5-[2-(2,6-diamino-4-hydroxypyrimidin-5-yl)ethyl]thien-2-ylcarboxylic acid; and 5-[6-(2,6-diamino-4-hydroxypyrimidin-5-yl)hexyl]thien-2-ylcarboxylic acid, there are obtained N-(5-[1-(2,6-diamino-4-hydroxypyrimidin-5-yl)pent-4-yl]thien-2-ylcarboxy)-L-glutamic acid; N-(5-[3-(2,6-diamino-4-hydroxypyrimidin-5-yl)propyl]thien-2-ylcarboxy)-L-glutamic acid; N-(5-[2-(2,6-diamino-4-hydroxypyrimidin-5-yl)ethyl]thien-2-ylcarboxy)-L-glutamic acid; and N-(5-[6-(2,6-diamino-4-hydroxypyrimidin-5-yl)hexyl]-thien-2-ylcarboxy)-L-glutamic acid.

EXAMPLE 3

The thienylcarboxylic acid starting materials can be obtained according to the following procedure. A. A 500 mL round bottomed flask, equipped with a magnetic stirrer, reflux condenser, pressure equalizing addition funnel, gas inlet, and an ice bath, was charged with 3.25 g (1.0 eq) of methyl 4-(4-hydroxybutyl)thien-2-ylcarboxylate and 1.61 g (1.05 eq) of triethyl amine in 200 mL of anhydrous ethyl ether. The solution was stirred under nitrogen and brought to 0° C. To this was added dropwise 1.82 g (1.05 eq) of mesityl chloride. A precipitate immediately began to form and the mildly exothermic reaction mixture was brought gradually to room temperature. After 4 hours, 100 mL of water were added, bringing the precipitated salts into solution. The organic layer was separated, washed with water, dried (magnesium sulfate), and concentrated under reduced pressure. The residue was purified by flash chromatography eluting with 30% ethyl acetate/hexanes. Fractions homogeneous by thin layer chromatography for the major component were combined and concentrated under reduced pressure to give 4.12 g (93.0%) of methyl 4-(4-methylsulfonyloxybutyl)thien-2-ylcarboxylate as a yellow oil; IR (KBr, cm$^{-1}$) 3019, 1710, 1445, 1359, 1339, 1260, 1206, 1175, 972, 937: UV (Ethanol): $\lambda_{max}$=288 nm (epsilon=6490), 248 nm (epsilon=10,100); $^1$H NMR (CDCl$_3$, 300 MHz) delta 7.60 (s, 1H), 7.15 (s, 1H), 4.21 (t, J=5.6 Hz, 2H), 3.84 (s, 3H), 2.98 (s, 3H), 2.64 (t, J=6.7 Hz, 2H), 1.69–1.75 (m, 4H); MASS: M+ =292 (EICEC).

Anal. Calcd. for C$_{11}$H$_{16}$O$_5$S$_2$: C, 45.19; H, 5.52; S, 21.93. Found: C, 45.43; H, 5.26; S, 21.91.

There is similarly prepared from methyl 5-(4-hydroxybutyl)thien-2-ylcarboxylate, methyl 5-(4-methylsufonyloxybutyl)-thien-2-ylcarboxylate; IR (KBr, cm$^{-1}$): 1708, 1463, 1359, 1341, 1296, 1276, 1225, 1220, 1216, 1215, 1174, 1100, 972, 936; UV (Ethanol): $\lambda_{max}$=277 nm (epsilon=11,900), 254 nm (epsilon=9150); $^1$H NMR (CDCl$_3$, 300 MHz) delta 7.63 (d, J=3.7 9150); Hz, 1H), 6.81 (d, J=3.7 Hz, 1H), 4.25 (t, J=5.6 Hz, 2H), 3.86 (s, 3H), 3.01 (s, 3H), 2.90 (t, J=6.6 Hz, 2H), 1.80–1.86 (m, 4H); MASS: M+ =292 (EICEC).

Anal. Calcd. for C$_{11}$H$_{16}$O$_5$S$_2$: C, 45.19; H, 5.52; S, 21.93. Found: C, 45.36; H, 5.37; S, 21.81.

In a similar fashion from methyl 4-(4-hydroxy-butyl)-thien-3-ylcarboxylate, methyl 4-(1-hydroxypent-4-yl)thien-2-ylcarboxylate; methyl 4-(3-hydroxypropyl)-thien-2-ylcarboxylate; methyl 4-(2-hydroxyethyl)thien-2-ylcarboxylate, methyl 4-(6-hydroxyhexyl)thien-2-ylcarboxylate; methyl 5-(4-hydroxybutyl)thien-3-ylcarboxylate; methyl 5-(1-hydroxypent-4-yl)thien-2-ylcarboxylate; methyl 5-(3-hydroxypropyl)thien-2-ylcarboxylate; methyl 5-(2-hydroxyethyl)thien-2-ylcarboxylate; and 5-(6-hydroxyhexyl)thien-2-ylcarboxylate, there are respectively obtained methyl 4-(4-methylsulfonyloxybutyl)thien-3-ylcarboxylate, methyl 4-(1-methylsulfonyloxypent-4-yl)thien-2-ylcarboxylate; methyl 4-(3-methylsulfonyloxypropyl)thien-2-ylcarboxylate; methyl 4-(2-methylsulfonyloxyethyl)thien-2-ylcarboxylate, methyl 4-(6-methylsulfonyloxyhexyl)thien-2-ylcarboxylate; methyl 5-(4-methylsulfonyloxybutyl)thien-3-ylcarboxylate; methyl 5-(1-methylsulfonyloxypent-4-yl)-2-ylcarboxylate; methyl 5-(3-methylsulfonyloxypropyl)thien-2-ylcarboxylate; methyl 5-(2-methylsulfonyloxyethyl)thien-2-ylcarboxylate; and 5-(6-methylsulfonyloxyhexyl)thien-2-ylcarboxylate.

B. A 250 Ml three-neck round bottom flask, equipped with a magnetic stirrer, reflux condenser, addition funnel, and gas inlet, was charged with 0.59 g (1.1 eq) of 60% sodium hydride and flame dried under a nitrogen atmosphere. After cooling to room temperature, mineral oil was removed by washing twice with anhydrous tetrahydrofuran and 100 mL of anhydrous tetrahydrofuran were then added. This mixture was brought to 0° C. on an ice bath and an anhydrous tetrahydrofuran solution of 1.52 g (1.0 eq) of ethyl cyanoacetate was added dropwise under a nitrogen atmosphere with moderation of evolution of hydrogen gas. The mixture was stirred vigorously while warming to room temperature until gas evolution was no longer observed. To this mixture, an anhydrous tetrahydrofuran solution of 3.92 g (1.0 eq) of methyl 4-(4-methylsulfonyloxybutyl)thien-2-ylcarboxylate was added dropwise. The resulting mixture was refluxed with stirring under a nitrogen atmosphere for 24 hours. After cooling to room temperature, solvent was removed under reduced pressure and diethyl ether was added to the residue. The organic extract was washed with water, brine, dried (magnesium sulfate), filtered and concentrated under reduced pressure. The residue was purified by flash chromatography eluting with 1:1 ethyl acetate:hexanes. Fractions homogeneous by thin layer chromatography for the major component were combined and concentrated under reduced pressure to give 1.98 g (47.7%) of pure methyl 4-(5-cyano-5-carbethoxypentyl)thien-2-carboxylate as a clear oil; IR (KBr, cm$^{-1}$): 1746, 1711, 1444, 1260, 1225, 1220, 1207; UV (Ethanol): $\mu_{max}$=280 nm (epsilon=5940), 248 nm (epsilon=9290); $^1$H NMR (CDCl$_3$, 300 MHz) delta 7.60 (s, 1H), 7.15 (s, 1H), 4.23, (q, J=7.2 Hz, 2H), 3.85 (s, 3H), 3.47 (t, J=6.9 Hz, 1H), 2.62 (t, J=7.5 Hz, 2H), 1.95 (q, J=7.3 Hz, 2H), 1.62–1.69 (m, 2H), 1.48–1.47 (m, 2H), 1.27–1.33 (m, 3H); MASS: M$^+$=309 (FD).

Anal. Calcd. for C$_{15}$H$_{19}$NO$_4$S: C, 58.23; H, 6.19; N, 4.53; S, 10.36. Found: C, 58.45; H, 6.33; N, 4.71; S, 10.28.

In a similar fashion, there is obtained from methyl 5-(4-methylsulfonyloxybutyl)thien-2-ylcarboxylate the corresponding methyl 5-(5-cyano-5-carbethoxypentyl)-thien-2-carboxylate; IR (KBr, cm$^{-1}$): 3020, 1745, 1708, 1464, 1296, 1270, 1225, 1223; 1220, 1213, 1207, 1100; UV (Ethanol: $\lambda_{max}$=278 nm (epsilon=11,900), 254 nm (epsilon=9070); $^1$H NMR (CDCl3, 300 MHz) delta 7.63 (d, J=7.3 Hz, 1H), 6.79 (d, J=7.3 Hz, 1H), 4.21–4.30 (m, 2H), 3.86 (s, 3H), 3.50 (t, J=6.9 Hz, 1H), 2.86 (q, J=7.4 Hz, 2H), 1.94–2.17 (m, 2H), 1.55–1.80 (m, 4H), 1.26–1.35 (m, 3H); MASS: M$^+$=309 (EICEC).

Likewise from methyl 4-(4-methylsulfonyloxybutyl)-thien-3-ylcarboxylate, methyl 4-(1-methylsulfonyloxypent-4-yl)thien-2-ylcarboxylate; methyl 4-(3-methylsulfonyloxypropyl)thien-2-ylcarboxylate; methyl 4-(2-methylsulfonyloxyethyl)thien-2-ylcarboxylate, methyl 4-(6-methylsulfonyloxyhexyl)thien-2-ylcarboxylate; methyl 5-(4-methylsulfonyloxybutyl)thien-3-ylcarboxylate; methyl 5-(1-methylsulfonyloxypent-4-yl)thien-2-ylcarboxylate; methyl 5-(3-methylsulfonyloxypropyl)-thien-2-ylcarboxylate; methyl 5-(2-methylsulfonyloxyethyl)thien-2-ylcarboxylate; and 5-(6-methylsulfonyloxyhexyl)-thien-2-ylcarboxylate, there can be obtained methyl 4-(5-cyano-5-carbethoxypentyl)thien-3-ylcarboxylate; methyl 4-(1-cyano-1-carbethoxyhex-5-yl)thien-2-ylcarboxylate; methyl 4-(4-cyano-4-carbethoxybutyl)thien-2ylcarboxylate; methyl 4-(3-cyano-3-carbethoxypropyl)-thien-2-ylcarboxylate; methyl 4-(7-cyano-7-carbethoxy-heptyl)thien-2-ylcarboxylate; methyl 5-(5-cyano-5-carbethoxypentyl)thien-3-ylcarboxylate; methyl 5-(1-cyano-1-carbethoxyhex-5-yl)thien-2-ylcarboxylate; methyl 5-(4-cyano-4-carbethoxybutyl)thien-2-ylcarboxylate; methyl 5-(3-cyano-3-carbethoxypropyl)thien-2-ylcarboxylate and methyl 5-(7-cyano-7-carbethoxyheptyl)thien-2-ylcarboxylate. C. A 250 mL round bottomed flask, equipped with a magnetic stirrer and gas inlet, was charged with 0.15 g (1.1 eq) of sodium metal and flame dried under a nitrogen atmosphere. After cooling to room temperature, 100 mL of methanol was added and the mixture stirred under a nitrogen atmosphere until all of the sodium had dissolved. At this time, 0.60 g (1.1 eq) of guanidine hydrochloride was added and stirring continued for 0.5 hour. To the solution was added a methanol solution of 1.78 g (1.0 eq) of methyl 4-(5-cyano-5-carbethoxypentyl)thien-2-ylcarboxylate. The reaction mixture was refluxed with stirring under a nitrogen atmosphere for 24 hours. After cooling to room temperature, volatiles were removed under reduced pressure and the residue was triturated in ether. The solid was collected by vacuum filtration and washed copiously with water on the filter pad. Purification was carried out by flash chromatography eluting with 10% methanol/chloroform. Fractions homogeneous by thin layer chromatography for the major component were combined and concentrated under reduced pressure to give 0.48 g (25.9%) of methyl 4-[4-(2,6-diamino-4-hydroxypyrimidin-5-yl)butyl]thien-2-ylcarboxylate as a white powder m.p.: 185°–186° C.; IR (KBr, cm$^{-1}$): 1696, 1672, 1622, 1602, 1442, 1430, 1385, 1259; UV (Ethanol): $\lambda_{max}$=278 nm (epsilon=17,800), 247 nm (epsilon=13,900), 210 nm (epsilon=22,600); $^1$H NMR (d$_6$-DMSO, 300 MHz) delta 9.68 (bs, 1H), 7.60 (s, 1H), 7.51 (s, 1H), 5.84 (bs, 2H), 5.59 (bs, 2H), 3.70 (s, 3H), 2.56 (t, J=7.2 Hz, 2H), 2.14 (t, J=7.4 Hz, 2H), 1.49–1.54 (m, 2H), 1.20–1.30 (m, 2H); MASS: M$^+$=322 (FD).

Anal. Calcd. for C$_{14}$H$_{18}$N$_4$O$_3$S: C, 52.16; H, 5.63; N, 7.38; S, 9.94. Found: C, 52.49; H, 5.54; N, 15.94; S, 9.60.

In an analogous fashion from methyl 5-(5-cyano-5-carbethoxypentyl)thien-2-ylcarboxylate there is obtained methyl 5-[4-(2,6-diamino-4-hydroxypyrimidin-5-yl)butyl]thien-2-ylcarboxylate, m.p.: 180°–181° C.; IR (KBr, cm$^{-1}$): 3391, 1709, 1689, 1618, 1602, 1460, 1447, 1437, 1426, 1304, 1297, 1271, 1101; UV (Ethanol): max$_1$=278 nm (epsilon=23,600), 210 nm (epsilon=23,700);$^1$H NMR (d$_6$-DMSO, 300 MHz) delta 9.66 (bs, 1H), 7.58 (d, J=7 Hz, 1H), 6.89 (d, J=3.7 Hz, 1H), 5.82 (bs, 2H), 5.58 (bs, 2H), 3.73 (s, 3H), 2.79 (t, J=7.6 Hz, 2H), 13 (t, J=7.3 Hz, 2H), 1.50–1.59 (m, 2H), 1.27–1.35 (m, 2H); MASS: M$^+$=322 (FD).

Anal. Calcd. for C$_{14}$H$_{18}$N$_4$O$_3$S: C, 52.16; H, 5.63; N, 7.38; S, 9.60. Found: C, 52.49; H, 5.54; N, 15.94; S, 9.60.

Similarly prepared from methyl 4-(5-cyano-5-carbethoxypentyl)thien-3-ylcarboxylate; methyl 4-(1-cyano-1-carbethoxyhex-5-yl)thien-2-ylcarboxylate; methyl 4-(4-cyano-4-carbethoxybutyl)thien-2-ylcarboxylate; methyl 4-(3-cyano-3-carbethoxypropyl)thien-2-ylcarboxylate; methyl 4-(7-cyano-7-carbethoxyheptyl)thien-2-ylcarboxylate; methyl 5-(5-cyano-5-carbethoxypentyl)thien-3-ylcarboxylate; methyl 5-(1-cyano-1-carbethoxyhex-5-yl)thien-2-ylcarboxylate; methyl 5-(4-cyano-4-carbethoxybutyl)thien -carbethoxyheptyl)thien-2ylcarboxylate, are methyl 4-[4-(2,6-diamino-4-hydroxypyrimidin-5-yl)butyl]thien-3-ylcarboxylate; methyl 4-[1-(2,6- diamino-4-hydroxypyrimidin-5-yl)pent-4-yl]thien-2-ylcarboxylate; methyl 4-[3-(2,6-diamino-4-hydroxypyrimidin-5-yl)propyl]thien-2-ylcarboxylate; methyl 4-[2-(2,6-diamino-4-hydroxypyrimidin-5-yl)ethyl]thien-2-ylcarboxylate; methyl 4-[6-(2,6-diamino-4-hydroxypyrimidin-5-yl)hexyl]-thien-2-ylcarboxylate; methyl 5-[4-(2,6-diamino-4-hydroxypyrimidin-5-yl)butyl]thien-3-ylcarboxylate; methyl 5-[1-(2,6-diamino-4-hydroxypyrimidin-5-yl)pent-4-yl]thien-2-ylcarboxylate; methyl 5-[3-(2,6-diamino-4 -hydroxypyrimidin-5-yl)propyl]thien-2-ylcarboxylate; methyl 5-[2-(2,6-diamino-4-hydroxypyrimidin-5-yl)ethyl]-thien-2-ylcarboxylate; and methyl 5-[6-(2,6-diamino-4-hydroxypyrimidin-5-yl)hexyl]thien-2-ylcarboxylate. D. A 50 mL round bottomed flask equipped with a magnetic stirrer was charged with 0.25 g of methyl 4-[4-(2,6-diamino-4-hydroxypyrimidin-5-yl)butyl]thien-2-ylcarboxylate in 30 mL of 1N sodium hydroxide and 5 mL of methanol. The reaction mixture was stirred at room temperature under mild heat for 18 hours. The homogeneous solution was acidified to pH 4 with hydrochloric acid and the resultant precipitate filtered, washed with water, and dried to give 0.23 g (91.3%) of 4-[4-(2,6-diamino-4-hydroxypyrimidin-5-yl)butyl]thien-2-ylcarboxylic acid as a white powder, m.p.: 258°–259° C.; IR (KBr, cm$^{-1}$): 2540, 2538, 2534, 2520, 2509, 1696, 1653, 1617, 1547, 1461, 1406, 1377, 1366, 1298, 1280; UV (Ethanol):$\lambda_{max}$=277 nm (epsilon=16,900), 246 nm (epsilon=12,900), 210 nm (epsilon=22,500); $^1$H NMR (d$_6$-DMSO, 300 MHz) delta 7.53 (s, 1H), 7.45 (s, 1H), 6.67 (bs, 2H), 6.14 (bs, 2H), 2.55 (t, J=7.3 Hz, 2H), 2.17 (t, J=7.3 Hz, 2H), 1.47–1.54 (m, 2H), 1.26–1.33 (m, 2H); MASS: M+=308 (FD).

Anal. Calcd. for C$_{13}$H$_{16}$N$_4$O$_3$S: C, 50.64; H, 5.23; N, 18.17; S, 10.40. Found: C, 53.17; H, 5.98; N, 15.31; S, 10.22.

Similarly prepared is 5-[4-(2,6-diamino-4-hydroxypyrimidin-5-yl)butyl]thien-2-ylcarboxylic acid, m.p.: 258°–259° C.; IR (KBr, cm$^{-1}$) 3185, 2947, 1695, 1664, 1645, 1600, 1536, 1461; UV (Ethanol): $\lambda_{max}$=277 nm (epsilon =22,200), 210 nm (epsilon=21,100); $^1$H NMR (d$_6$-DMSO, 300 MHz) delta 7.51 (d, J=3.7 Hz, 1H), 7.49, (bs, 2H), 6.85 (d, J=3.7 Hz, 1H), 6.73 (bs, 2H), 2.77 (t, J=7.4 Hz, 2H), 2.19 (t, J=7.0 Hz, 2H), 1.51–1.59 (m, 2H), 1.30–1.37 (m, 2H); MASS: M+=308 (FD).

In a like fashion, from methyl 4-[4-(2,6-diamino-4-hydroxypyrimidin-5-yl)butyl]thien-3-ylcarboxylate; methyl 4-[1-(2,6-diamino-4-hydroxypyrimidin-5-yl)-pent-4-yl]thien-2-ylcarboxylate; methyl 4-[3-(2,6-diamino-4-hydroxypyrimidin-5-yl)propyl]thien-2-ylcarboxylate; methyl 4-[2-(2,6-diamino-4-hydroxypyrimidin-5-yl)ethyl]thien-2-ylcarboxylate; methyl 4-[6-(2,6-diamino-4-hydroxypyrimidin-5-yl)hexyl]thien-2-ylcarboxylate; methyl 5-[4-(2,6-diamino-4-hydroxypyrimidin-5-yl)butyl]thien-3-ylcarboxylate; methyl 5-[1-(2,6-diamino-4-hydroxypyrimidin-5-yl)pent-4-yl]thien-2-ylcarboxylate; methyl 5-[3-(2,6-diamino-4-hydroxypyrimidin-5-yl)propyl]thien-2-ylcarboxylate; methyl 5-[2-(2,6-diamino-4-hydroxypyrimidin-5-yl)ethyl]thien-2-ylcarboxylate; and methyl 5-[6-(2,6-diamino-4-hydroxypyrimidin-5-yl)hexyl]thien-2-ylcarboxylate, there are respectively obtained 4-[4(2,6-diamino-4-hydroxypyrimidin-5-yl)butyl]thien-3-ylcarboxylic acid; 4-[1-(2,6-diamino-4-hydroxypyrimidin-5-yl)pent-4-yl]thien-2-ylcarboxylic acid; 4-[3-(2,6-di-amino-4-hydroxypyrimidin-5-yl)propyl]thien-2-ylcarboxylic acid; 4-[2-(2,6-diamino-4-hydroxypyrimidin-5-yl)ethyl]-thien-2-ylcarboxylic acid; 4-[6-(2,6-diamino-4-hydroxypyrimidin-5-yl)hexyl]thien-2-ylcarboxylic acid; 5-[4-(2,6-diamino-4-hydroxypyrimidin-5-yl)butyl]thien3-ylcarboxylic acid; 5-[1-(2,6-diamino-4-hydroxypyrimidin-5-yl)pent-4-yl]thien-2-ylcarboxylic acid; 5-[3-(2,6-diamino-4-hydroxypyrimidin-5-yl)propyl]thien-2-ylcarboxylic acid; 5-[2-(2,6-diamino-4-hydroxypyrimidin5-yl)ethyl]thien-2-ylcarboxylic acid; and 5-[6-(2,6-diamino-4-hydroxypyrimidin-5-yl)hexyl]thien-2-ylcarboxylic acid.

EXAMPLE 4

The hydroxyalkylthienylcarboxylates can be obtained according to the following procedures.

A 50 mL round bottom flask, equipped with a magnetic stirrer and gas inlet, was charged with 0.8 mg (0.005 eq) of palladium chloride, 2.3 mg (0.01 eq) of triphenylphosphine, 1.6 mg of copper (1) iodide, 0.19 g of methyl 4-bromothien-2-ylcarboxylate (obtained by oxidation of 4-bromothien-2-ylaldehyde followed by esterification), 0.43 g of triethylamine, and 0.06 g of 3-but-yn-1-ol in 20 mL of acetonitrile under a nitrogen atmosphere. The reaction mixture was heated at reflux with stirring under a nitrogen atmosphere for 18 hours. After cooling to room temperature, volatiles were removed under reduced pressure and the residue was partitioned between chloroform and water. The organic extract was washed with water (2×), brine, dried (sodium sulfate), filtered and concentrated in vacuo. The residue was purified by flash chromatography eluting with 2:1 hexane/ethyl acetate. Fractions homogeneous by thin layer chromatography for the major component were combined and concentrated under reduced pressure to give 0.12 g (66.7%) of methyl 4-(4-hydroxybut-yn-1-yl)thien-2-ylcarboxylate as a yellow oil; IR (KBr, cm$^{-1}$): 3025 3021, 3015, 1713, 1446, 1293, 1261, 1231, 1228, 1225, 1222, 1214, 1192, 1080, 1053; UV (Ethanol):- $\lambda_{max}$=294 nm (epsilon=3680), 228 nm (epsilon=26,900); $^1$H NMR (CDCl$_3$, 300 MHz) delta 7.72 (s, 1H), 7.53 (s, 1H), 3.87 (s, 3H), 3.79 (t, J=6.2 Hz, 2H), 2.65 (t, J=6.3 Hz, 2H), 1.87 (bs, 1H); MASS: M+=210 (EICEC).

Anal. Calcd. for C$_{10}$H$_{10}$O$_3$S: C, 57.13; H, 4.79; S, 15.25. Found: C, 54.50; H, 4.77; S, 14.95.

A Parr flask was charged with 4.00 g of methyl 4-(4-hydroxybut-1-yn-1-yl)thien-2-ylcarboxylate in 100 mL of ethanol. Then 2.00 g (50% wt eq) of 5% palladium on charcoal was added. Parr hydrogenation was carried out at 50 psi of hydrogen for 6 hours. The reaction mixture was filtered through a Celite pad which was washed with ethanol. The filtrate was concentrated under reduced pressure to give 3.34 g (81.9%) of methyl 4-(4-hydroxybutyl)thien-2-ylcarboxylate as a clear oil; IR (KBr, cm$^{-1}$): 1710, 1444, 1293, 1260, 1225; UV (Ethanol) :$\lambda_{max}$=281 nm (epsilon=6450), 248 nm (epsilon=10,100); $^1$H NMR (CDCl3, 300 MHz) delta 7.59 (s, 1H), 7.12, (s, 1H), 3.81 (s, 3H), 3.60 (t, J=6.3 Hz, 2H), 2.59 (t, J=7.4 Hz, 2H), 2.10 (bs, 1H), 1.60–1.68 (m, 2H), 1.51–1.58 (m, 2H); MASS: M+=2148 (EICEC).

Anal. Calcd. for C$_{10}$H$_{14}$O$_3$S: C, 56.05; H, 6.59; S, 14.96. Found: C, 55.83; H, 6.76; S, 14.91.

Methyl 5-(4-hydroxybutyl)thien-2-ylcarboxylate is obtained in a similar fashion; IR (KBr, cm$^{-1}$): 1707, 1462, 1297, 1272, 12243, 1100; UV (Ethanol): max$_1$=278 nm (epsilon=12,000), 254 nm (epsilon=8910); $^1$H NMR (CDCl$_3$, 300 MHz) delta 7.62 (d, J=3.7 Hz, 1H), 6.80 (d, J=3.7 Hz, 1H), 3.85 (s, 3H), 3.67 (t, J=6.3 Hz, 2H), 2.87 (t, J=7.4 Hz, 2H), 1.73–1.81 (m, 2H), 1.61–1.68 (m, 3H); MASS: M+=214 (EICEC).

What is claimed is:

1. A compound of the formula:

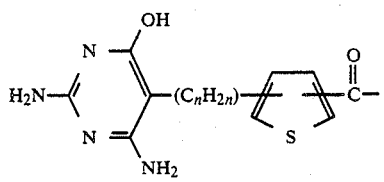

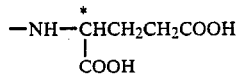

in which n has a value of 2 to 6; and the configuration about the carbon atom designated * is L; and the pharmaceutically acceptable salts thereof.

2. A compound according to claim 1 in which n has a value of 3 to 5.

3. A compound according to claim 2 in which n is 4.

4. The compound according to claim 1 which is N-(4-[4-(2,6-diamino-4-hydroxypyrimidin-5-yl)butyl]thien-2-ylcarboxy)-L-glutamic acid.

5. The compound according to claim 1 which is N-(5-[4-(2,6-diamino-4-hydroxypyrimidin-5-yl)butyl]thien-2-ylcarboxy)glutamic acid.

6. The method of combating neoplastic growth in a mammal which comprises administering to the mammal in a single or multiple dose regimen an effective amount of a compound according to claim 1.

7. A pharmaceutical composition for combating neoplastic growth in a mammal which comprises an amount of a compound according to claim 1 which upon administration to the mammal in a single or multiple dose regimen is effective to combat said growth, in combination with a pharmaceutically acceptable carrier.